United States Patent
Luo

(10) Patent No.: US 11,746,092 B2
(45) Date of Patent: Sep. 5, 2023

(54) SYNTHETIC METHOD AND APPLICATION OF 2-HYDROXYPHENYL-5-PYRAZINYL KETONE

(71) Applicants: Intelligent Manufacturing Institute of Hefei University of Technology, Hefei (CN); Hefei University of Technology, Hefei (CN)

(72) Inventor: Mei Luo, Hefei (CN)

(73) Assignees: Intelligent Manufacturing Institute of Hefei University Technology, Anhui (CN); Hefei University of Technology, Anhui (CN)

( * ) Notice: Subject to any disclaimer, the term of this patent is extended or adjusted under 35 U.S.C. 154(b) by 173 days.

(21) Appl. No.: 17/388,067

(22) Filed: Jul. 29, 2021

(65) Prior Publication Data

US 2022/0033362 A1  Feb. 3, 2022

(30) Foreign Application Priority Data

Jul. 29, 2020 (CN) .......................... 202010745514.5
Sep. 17, 2020 (CN) .......................... 202010982583.8

(51) Int. Cl.
  *C07D 239/26* (2006.01)
  *B01J 31/02* (2006.01)

(52) U.S. Cl.
  CPC ........ *C07D 239/26* (2013.01); *B01J 31/0244* (2013.01)

(58) Field of Classification Search
  None
  See application file for complete search history.

(56) References Cited

FOREIGN PATENT DOCUMENTS

CN  111018776  *  2/2020  .......... C07D 213/85

OTHER PUBLICATIONS

Farooq et al, J of Heterocyclic Chem, vol. 58: pp. 1209-1224, https://doi.org/ 10.1002/jhet.4226 (Year: 2021).*
Ojima et al, Chemical Society of Japan, pp. 331-334 (Year: 1975).*

* cited by examiner

*Primary Examiner* — Zinna Northington Davis
(74) *Attorney, Agent, or Firm* — Thomas | Horstemeyer, LLP

(57) ABSTRACT

A method of synthesizing a 2-hydroxyphenyl-5-pyrimide ketone represented by the following chemical formula (I), including: weighing 0.048 g of a palladium complex, 0.8413 g of chromone-3-formaldehyde and 2.5719 g of ammonium formate into a 100 mL round bottom flask, then adding 50 mL of anhydrous methanol to dissolve, heating to reflux for 36 h, then stopping the reaction, performing column chromatography with petroleum ether and dichloromethane in a volume ratio of 1:1, and then naturally volatilizing the first component to obtain a light yellow crystal, namely the 2-hydroxyphenyl-5-pyrimidine ketone;

wherein the chemical formula of the compound (I) is as follows:

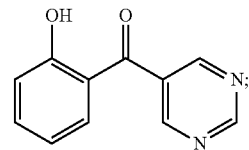

(I)

and an use of compound (I) as a catalyst in the reaction of benzophenone imine and trimethylsilyl nitrile showing a good catalytic performance, with a conversion rate of 69.1%.

2 Claims, 1 Drawing Sheet

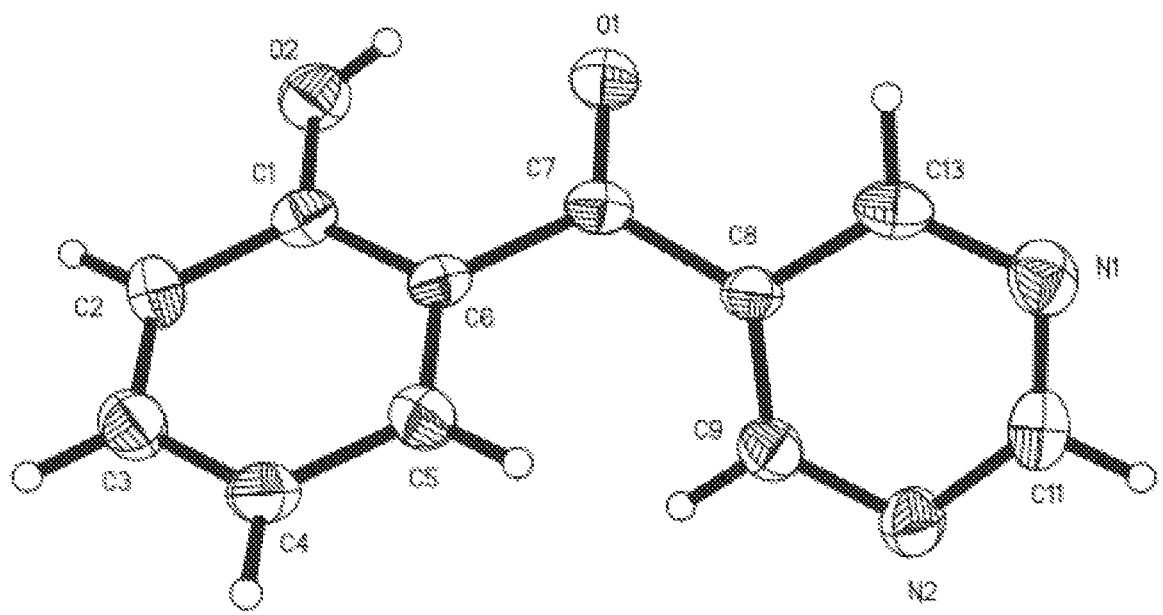

SYNTHETIC METHOD AND APPLICATION OF 2-HYDROXYPHENYL-5-PYRAZINYL KETONE

CROSS REFERENCE TO RELATED APPLICATION

This patent application claims the benefit and priority of Chinese Patent Application No. 202010745514.5 filed on Jul. 29, 2020, and of Chinese Patent Application No. 202010982583.8 filed on Sep. 17, 2020, the disclosures of which are incorporated by reference herein in its entirety as part of the present application.

TECHNICAL FIELD

The present disclosure relates to a method for preparing a compound, more particularly to a method and use of a pyrimidine derivative, and exactly to a synthetic method and use of 2-hydroxyphenyl-5-pyrimidine ketone.

BACKGROUND ART

The synthetic method of 2-hydroxyphenyl-5-pyrimidine ketone has been reported by a large number of literatures, see references 1-2:

REFERENCES

1. Unusual transformation of substituted-3-formyl-chromones topyrimidine analogues: Synthesis and antimicrobial activities of 5-(o-hydroxyaroyl) pyrimidines, Raj, Tilak et al, Bioorganic & Medicinal Chemistry Letters, 23 (22), 6093-6096; 2013.
2. Synthesis of 5H-[1] benzopyrano [4, 3-D] pyrimidin-5-one, Loewe, W., Synthesis, (4), 274; 1976.

SUMMARY

In the present disclosure, the reaction of chromone-3-formaldehyde with ammonium formate is catalyzed by a 1 mol % palladium complex using anhydrous methanol as a solvent to obtain a compound. The technical problem to be solved is to synthesize the target product in one step.

(A) The compounds referred to herein are compounds represented by the following chemical formula (I):

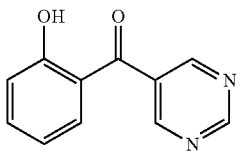 [SMILES: O=C(c1cncnc1)c1ccccc1O]

Chemical name: 2-hydroxyphenyl-5-pyrimidine ketone, referred to as compound (I).

The synthetic method of the compound (I) includes synthesis and separation, the synthesis is as follows: weighing 0.048 g of palladium complex, 0.8413 g of chromone-3-formaldehyde and 2.5719 g ammonium formate and placing in a 100 ml round bottom flask, then adding 50 mL of anhydrous methanol to dissolve, heating for reflux for 36 h, then stopping the reaction, performing column chromatography with petroleum ether and dichloromethane in a volume ratio of 1:1, and then naturally volatilizing the first component to obtain a light yellow crystal.

The synthesis reaction is as follows:

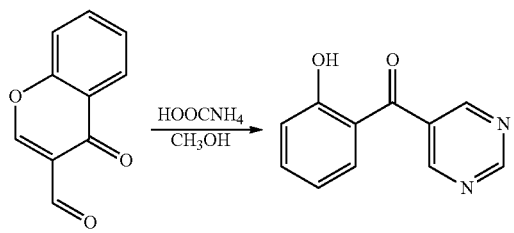

The synthetic method obtains the target product in one step, which has simple process and convenient operation.

The reaction mechanism can be speculated as follows: Under the action of 1 mol % palladium complex, the cyclic ether of chromone-3-carboxaldehyde is firstly decomposed, and then reacted with ammonium formate to obtain 2-hydroxyphenyl-5-pyrimidine ketone in one step.

BRIEF DESCRIPTION OF THE DRAWINGS

FIGURE shows a crystal X-ray diffraction analysis of 2-hydroxyphenyl-5-pyrimidine ketone.

DETAILED DESCRIPTION OF THE EMBODIMENTS

1. Preparation of Chiral Palladium Complexes (1) Preparation of [1,4-(4R)-diisopropyl-2-oxazolinyl] benzene In a 100 mL two-neck flask, under anhydrous and oxygen-free conditions, 1.4054 g (10.64 mmol) of anhydrous $ZnCl_2$, 40 ml of chlorobenzene, 5.0236 g (39.2 mmol) of 1,4-dicyanobenzene, and 16.2075 g of L-valinol were added, the mixture was refluxed at high temperature for 60 h, the reaction was stopped, and the solvent was removed under reduced pressure. The residue was dissolved in water and extracted with $CHCl_3$ (20 mL×2). The organic phase was dried with anhydrous sodium sulfate, and the solvent was removed by rotating. The crude product was subjected to column chromatography with petroleum ether/dichloromethane (4:1) to obtain a light green viscous liquid with a yield of 52%; white crystals, melting point: 48-50° C., $[\alpha]^5_D$=+111.9° (c=0.429, $CHCl_3$); $^1$HNMR (500 MHz, $CDCl^3$, 27° C.), δ (ppm)=7.97 (s, 4H), 4.39-4.43 (t, 3.18 Hz, 1H), 4.09-4.15 (m, 2H), 1.85-1.86 (m, 1H), (d, J=6.24 Hz, 6H), 0.86-0.96 (d, J=6.24 Hz, 6H). $^{13}$CNMR 18.13, 19.03, 32.85, 70.26, 72.76, 128.10, 128.16, 130.32, 162.82. IR: 3273, 2976, 2960, 2932, 2889, 2869, 1643, 1512, 1469, 1408, 1382, 1366, 1350, 1320, 1296, 1276, 1214, 1180, 1108, 1077, 1047, 1014, 971, 955, 900, 891, 838, 726, 698, 675, 659, 540. HRMS (EI): m/z (%): calcd for $C_{18}H_{24}N_2O_2$: 300.1838; found: 300.1833.

(2) Preparation of bis{[1,4-(4S)-diisopropyl-2-oxazolinylbenzene] palladium chloride} complex In a 100 mL two-neck flask, under anhydrous and oxygen-free conditions, 1.5603 g (4.92 mmol) of palladium chloride, 1.0435 g (3.48 mmol) of 1,4-(4R)-diisopropyl-2-oxazolinyl-benzene, 30 mL of chlorobenzene were added, the mixture was refluxed at high temperature for 48 h, then the reaction was stopped, and the solvent was removed under reduced pressure. The residue was dissolved in chloroform and ethanol, and the solvent was volatilized naturally to obtain a crystal with reddish-brown complex with a yield of 92%; m.p.: >200° C. $[a]^5_D$=+512.8° (c 0.0564, CH$_3$OH); $^1$H NMR (600 MHz, CDCl$_3$), δ ppm 8.81 (s, 8H, ArH), 4.61-4.63 (m, 4H, CH×4), 4.53 (t, J=9.6 Hz, 4H, CH×4), 4.44 (t, J=8.5 Hz, 4H, CH×4), 3.07-3.10 (m, 4H), 1.18 and 1.15 (dd, J=6.7, 7.2 Hz, 24H, CH3×4); $^{13}$C NMR (150 MHz, CDCl$_3$) δ ppm 166.8, 130.1(×2), 129.3, 72.0, 69.1, 30.7, 19.0, 15.6; $v_{max}$ (cm$^{-1}$) 3487, 3049, 2957, 2929, 2872, 1642, 1609, 1572, 1509, 1480, 1464, 1416, 1379, 1331, 1288, 1246, 1178, 1141, 1123, 1099, 1045, 1018, 959, 933, 899, 854, 804, 770, 722, 693, 438; Elemental analysis for C$_{36}$H$_{48}$N$_4$Cl$_4$O$_4$Pd$_2$, found C 45.26%, H 5.06%, N 5.86%; requires C 45.32%, H 5.24%, N 5.48%;

2. Preparation of 2-hydroxyphenyl-5-pyrimidine ketone 0.048 g of palladium complex, 0.8413 g of chromone-3-formaldehyde and 2.5719 g of ammonium formate were weighed and put into a 100 mL round bottom flask, then 50 mL of anhydrous methanol was added to dissolve, heated to reflux for 36 h, then the reaction was stopped, the crude product was subjected to column chromatography with petroleum ether and dichloromethane in a volume ratio of 1:1, the first component was naturally volatilized to obtain the light yellow crystals. Crystal (I): yield: 52%; m.p.: 82-84° C.; FTIR (cm$^{-1}$) 3408, 3044, 1621, 1602, 1574, 1465, 1432, 1416, 1335, 1299, 1242, 1219, 1191, 1178, 1149, 1115, 1035, 1001, 964, 937, 919, 895, 863, 826, 767, 751, 715, 660, 631, 586; m.p.: 132-134° C.; $^1$H NMR (600 MHz, 298K, CDCl$_3$ and DMSO) δ 10.6 (s, 1H, OH), 9.32 (s, 1H), 9.0 (s, 2H), 7.48-7.49 (m, 2H), 6.96-6.99 (m, 2H); $^{13}$C NMR (150 MHz, 298K, CDCl$_3$ and DMSO-d6) δ 194.2, 160.7, 158.1, 157.3, 135.3, 131.7, 131.5, 123.5, 120.0, 117.5; Anal. Calcd. for C$_{11}$H$_8$N$_2$O$_2$(%): C, 66.00; H, 4.03; N, 13.99. Found: C, 65.87; H, 4.38; N, 13.65; HRMS for C$_{11}$H$_8$N$_2$O: Anal. Calcd.:200.0586; Found: 200.0596.

The crystal data of the compound crystal (I) is as follows:

| | |
|---|---|
| Empirical formula | C$_{11}$H$_8$N$_2$O$_2$ |
| Molecular weight | 200.19 |
| Temperature | 293 (2) K |
| Wavelength | 0.71073 Å |
| Crystal system, space group | Monoclinic system, P 21 21 21 |
| The unit cell parameter | a = 5.505 (2) Å α = 90°; |
| | b = 11.343 (10) Å β = 90° |
| | c = 14.796 (13) Å γ = 90° |
| Volume | 923.9 (5) Å^3 |
| Charge density | 4, 1.439 Mg/m^3 |
| Absorption correction parameter | 0.102 mm^−1 |
| Number of electrons in a unit cell | 416 |
| Crystal size | 0.170 × 0.140 × 0.040 mm |
| Range of theta angle | 2.753 to 25.487 |
| HKL's indicator collection range | −6 <= h <= 6, −13 < k <= 8, −16 < l <= 17 |
| Reflections collected/unique | 4688/1708 [R(int) = 0.1298] |
| Absorption correction method | Multi-layer scanning |
| Refinement method | F^2's matrix least squares method |
| Data/restraints/parameters | 1708/0/38 |
| Refinement method | 0.998 |
| Consistency factor of the diffraction points | R1 = 0.0742, ωR2 = 0.1360 |
| Coincidence factor of observable diffraction | R1 = 0.2024, ωR2 = 0.1865 |
| Largest diff. peak and valley | 0.252 and −0.253 e · Å−3 |

Typical bond length data for crystals:

| | |
|---|---|
| O (1)—C (7) | 1.228(7) |
| O (2)—C (1) | 1.356(8) |
| O (2)—H (2) | 0.8200 |
| N (1)—C (10) | 1.305(10) |
| N (1)—C (11) | 1.333(11) |
| N (2)—C (10) | 1.335(11) |
| N (2)—C (9) | 1.341(9) |
| C (1)—C (2) | 1.394(11) |
| C (1)—C (6) | 1.405(10) |
| C (2)—C (3) | 1.351(10) |
| C (2)—H (2A) | 0.9300 |
| C (3)—C (4) | 1.378(11) |
| C (3)—H (3) | 0.9300 |
| C (4)—C (5) | 1.388(11) |
| C (4)—H (4) | 0.9300 |
| C (5)—C (6) | 1.385(9) |
| C (5)—H (5) | 0.9300 |
| C (6)—C (7) | 1.501(12) |
| C (7)—C (8) | 1.482(11) |
| C (8)—C (9) | 1.366(9) |
| C (8)—C (11) | 1.386(12) |
| C (9)—H (9) | 0.9300 |
| C (10)—H (10) | 0.9300 |
| C (11)—H (11) | 0.9300 |

Typical bond angle data of crystals:

| | |
|---|---|
| C (1)—O (2)—H (2) | 109.5 |
| C (10)—N (1)—C (11) | 114.1(8) |
| C (10)—N (2)—C (9) | 113.7(8) |
| O (2)—C (1)—C (2) | 117.9(8) |
| O (2)—C (1)—C (6) | 122.8(8) |
| C (2)—C (1)—C (6) | 119.3(7) |
| C (3)—C (2)—C (1) | 120.2(9) |
| C (3)—C (2)—H (2A) | 119.9 |
| C (1)—C (2)—H (2A) | 119.9 |
| C (2)—C (3)—C (4) | 121.2(10) |
| C (2)—C (3)—H (3) | 119.4 |
| C (4)—C (3)—H (3) | 119.4 |
| C (3)—C (4)—C (5) | 119.9(9) |
| C (3)—C (4)—H (4) | 120.1 |
| C (5)—C (4)—H (4) | 120.1 |
| C (6)—C (5)—C (4) | 119.7(9) |
| C (6)—C (5)—H (5) | 120.1 |
| C (4)—C (5)—H (5) | 120.1 |
| C (5)—C (6)—C (1) | 119.5(8) |
| C (5)—C (6)—C (7) | 122.0(8) |
| C (1)—C (6)—C (7) | 118.5(7) |
| O (1)—C (7)—C (8) | 118.2(8) |
| O (1)—C (7)—C (6) | 121.0(8) |
| C (8)—C (7)—C (6) | 120.8(7) |
| C (9)—C (8)—C (11) | 116.1(8) |
| C (9)—C (8)—C (7) | 124.1(8) |
| C (11)—C (8)—C (7) | 119.4(8) |
| N (2)—C (9)—C (8) | 123.1(8) |
| N (2)—C (9)—H (9) | 118.5 |
| C (8)—C (9)—H (9) | 118.5 |
| N (1)—C (10)—N (2) | 129.8(10) |
| N (1)—C (10)—H (10) | 115.1 |
| N (2)—C (10)—H (10) | 115.1 |
| N (1)—C (11)—C (8) | 123.1(8) |
| N (1)—C (11)—H (11) | 118.4 |
| C (8)—C (11)—H (11) | 118.4 |

Use of the condensation reaction of benzophenone imine and trimethylsilyl nitrile

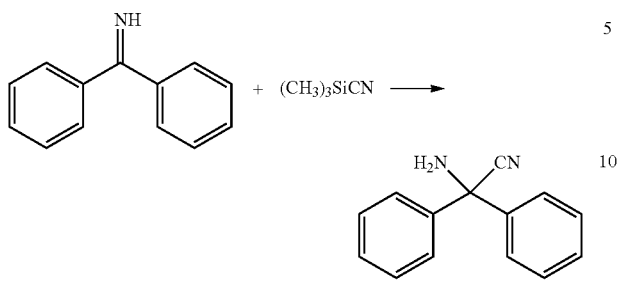

1 mmol of benzophenone imine and 0.2 mL of trimethylsilyl nitrile were weighed and placed into a 25 mL small flask, 2 mL of THF and 0.1 mmol of compound (I) were added, stirred at room temperature for 5 h, a small amount of sample was taken for NMR detection. The results show that the conversion rate is 69.1%, $^1$H-NMR (600 MHz, CDCl$_3$, 27° C.) δ 7.23-7.59 (m, 10H), 4.10 (s, 2H).

What is claimed is:

1. A method of synthesizing a 2-hydroxyphenyl-5-pyrimidine ketone represented by a chemical formula (I), comprising: weighing 0.048 g of a palladium complex, 0.8413 g of chromone-3-formaldehyde and 2.5719 g of ammonium formate into a 100 mL round bottom flask, then adding 50 mL of anhydrous methanol to dissolve, heating to reflux for 36 h, then stopping the reaction, performing column chromatography with petroleum ether and dichloromethane in a volume ratio of 1:1, and then naturally volatilizing a first component to obtain a light yellow crystal, namely the 2-hydroxyphenyl-5-pyrimidine ketone;

wherein the chemical formula (I) is as follows:

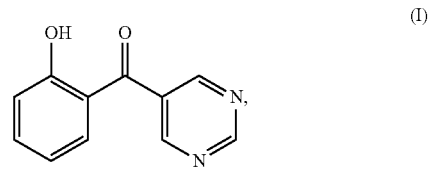 [SMILES: O=C(c1cncnc1)c1ccccc1O]

and
the light yellow crystal has crystal data as follows: orthorhombic system, a space group of P 21 21 21; unit cell parameters are a=5.505 (2) Å α=90°; b=11.343(10) Å β=90°; c=14.796(13) Å γ=90°, obtained by collecting diffraction data at a temperature of 273(2) K on an Oxford X-ray single crystal diffractometer using ω-θ scanning with CuKα rays 0.71073 Å, which is monochromatized by a graphite monochromator.

2. A method for condensation of benzophenone imine and trimethylsilyl nitrile, the method comprising: using a catalyst having a chemical formula (I),

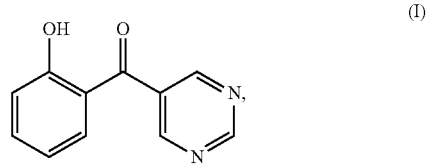 [SMILES: O=C(c1cncnc1)c1ccccc1O]

wherein a conversion rate is 69.1%.

* * * * *